United States Patent [19]

Mason

[11] Patent Number: 4,992,258
[45] Date of Patent: Feb. 12, 1991

[54] DENTRIFICE COMPOSITION

[75] Inventor: Stephen C. Mason, Colgate-Palmolive, Belgium

[73] Assignee: Colgate-Palmolive Company, New York, N.Y.

[21] Appl. No.: 425,538

[22] Filed: Oct. 23, 1989

[51] Int. Cl.$^5$ .............................................. A61K 7/16
[52] U.S. Cl. ...................................................... 424/49
[58] Field of Search ......................................... 424/49

[56] References Cited

U.S. PATENT DOCUMENTS 4,064,231 12/1977 Asakawa et al. ...................... 424/52
4,081,526 3/1978 Asakawa et al. ...................... 424/57

FOREIGN PATENT DOCUMENTS 0327776 8/1989 European Pat. Off. .

OTHER PUBLICATIONS

Asakawa et al., C.A. 86: 161331z (1977), Asakawa et al., C.A. 87: 44250g (1977). 3411 Lion Corp. C.A. 103: 109784e (1985).
Sato C.A. 111: 120662z (1989).

*Primary Examiner*—Shep K. Rose
*Attorney, Agent, or Firm*—Robert L. Stone; Murray M. Grill

[57] ABSTRACT

A dentifrice for treatment of hypersensitive dentine containing montmorrolinite clay.

10 Claims, No Drawings

DENTRIFICE COMPOSITION

This invention relates to dentifrice compositions and in particular to a dentifrice composition for treatment of hypersensitive dentine.

Hypersensitive dentine is a recognized problem and dentifrices have been described and sold to alleviate the problem. For example, dentifrice products with strontium chloride (U.S. Pat. No. 3,122,483) and potassium nitrate (U.S. Pat. No. 3,863,006) have been available. Soluble oxalate salts are described (U.S. Pat. Nos. 4,057,621 and 4,538,990) for treating exposed dental tubules and thereby reducing dentine permeability and sensitivity. Citric acid and sodium citrate are described (U.S. Pat. No. 4,011,309) to produce a non-ionized aqueous gel complex on the surface of dentine and, thus, protect or occlude dental tubules to reduce sensitivity. Strontium salt and fluoride are described to counter dentine hypersensitivity in European Patent Publication No. 200,323. Desensitizing sensitive teeth with a saturated solution of calcium chloride dehydrate, magnesium chloride hexahydrate, sodium chloride and potassium bicarbonate is described in U.S. Pat. No. 4,631,185. Apatite polishing material is described in U.S. Pat. No. 4,634,589 to reduce tooth hypersensitivity. Solubilized aluminum and Solubilized carboxylate are described in U.S. Pat. No. 4,645,662 to prevent and remedy dental hypersensitivity. In European Patent Application No. 278,744 triclosan and potassium salt is described as a combination against tooth sensitivity.

It is an advantage of this invention that a dentifrice composition which desensitizes hypersensitive teeth in a highly effective manner is provided.

It is a further advantage of this invention that a dentifrice composition is provided which effectively blocks exposed dentinal tubules to reduce the dentinal fluid flow rate through the tubules and thereby reduce tooth sensitivity.

Other advantages of this invention will be apparent from consideration of the following specification.

In accordance with certain of its aspects, this invention relates to a dentifrice comprising about 0.1-10% by weight of montmorillonite clay in a dentifrice vehicle.

In accordance with further of its aspects, this invention relates to method for desensitizing hypersensitive dentin by applying thereto a dentifrice composition comprising at least about 0.1% by weight of montmorillonite clay in a dentifrice vehicle.

Montmorillonite clays are incorporated into a dentifrice vehicle in amount of at least about 0.1% by weight. The upper amount is limited only by ability to effectively disperse the clay in the dentifrice and may be about 10% or more. The range is preferably about 0.5-5%, and most preferably about 1-3%. The clays have small particle size (less than 2 microns) and have a affinity for proteinaceous material. Without being bound by theory, it is possible that they are effective in reducing dentin hypersensitivity since dentine may have a substantial collagenous protein content and thus the clay may strongly adhere to and coat the dentine surface with an amorphous layer, thereby effectively blocking dentine tubules and reducing dentine permeability. Typical desirable montmorillonite clays are available from ECCA, Inc. as Gelwhile, for instance, Gelwhite L, Gelwhite H, Gelwhite NF and Gelwhite GP. Gelwhite GP is preferred. It is white in color, has a brightness of 80% (G.E.), contains 8% free moisture, has a pH of 10.0 in a 2% slurry and a viscosity of 5.0 as the percentage of solids required to obtain 800 cps in distilled water.

Reduction of dentin hypersensitivity can also be improved by incorporating in the dentifrice vehicle, in addition to the montmorillonite clay, about 0.1-3% by weight, preferably about 0.5-2.5%, and most preferably about 0.5-1.5%, of a polymeric polycarboxylate.

The polymeric carboxylates which can be utilized are typically anionic linear or crosslinked polymeric polycarboxylates having a molecular weight of about 1,000 to about 1,000,000, preferably in the form of water soluble alkali metal (potassium and sodium) or ammonium salts. The linear polycarboxylates are preferably 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example to Gantrez AN 139 (M.W. 500,000), A.N. 119 (M.W. 250,000) and, preferably, S-97 Pharmaceutical Grade (M.W. 70,000) from GAF Corporation. Other linear polymeric polycarboxylates include 1:1 copolymers of maleic anhydride with ethyl acrylate, hydroxyethyl methacrylate or methyl vinyl ether; 1:1 copolymers of acrylic acid with methyl or hydroxyethyl methacrylate, methyl or ethyl acrylate, iso-butyl vinyl ether or N-vinyl-2-pyrrolidone; copolymers of maleic anhydride with styrene, isobutylene or ethyl vinyl ether, polyacrylic, polyitaconic and polymaleic acids, and sulfoacrylic oligomers. The copolymers contain sufficient carboxylic salt groups for water-solubility.

The crosslinked polycarboxylates are preferably carboxyvinyl polymers made by B. F. Goodrich and designated by the trademarks Carbopol 934, Carbopol 940 and Carbopol 941. Each of these products consist essentially of a colloidal water soluble polymer of acrylic acid crosslinked with about 0.75 to 2.0% of a crosslinking agent selected from the class consisting of polyalkyl sucrose and polyalkyl pentaerythritol.

The dentifrice vehicle contains liquids and solids in a dentifrice. In general, the liquid comprises water and/or a humectant such as glycerin, sorbitol, propylene glycol or polyethylene glycol including suitable mixtures thereof. It is usually advantageous to use a mixture of both water and one or two humectants. The total liquid content is generally about 20-75% by weight of the vehicle. In transparent and translucent vehicles, the liquid content of the toothpaste may be about 20-75% by weight, while in opaque vehicles the total liquid content is usually about 20-60% by weight. The preferred humectants are glycerin and sorbitol.

The solid portion of the vehicle is a gelling agent. In the instant invention the gelling agent typically can be alkali metal carboxymethyl cellulose, hydroxy ethyl cellulose, and hydroxymethyl cellulose, xanthan gum, viscarin, iota carrageenan, gelatin, starch, glucose, sucrose, polyvinyl pyrollidone, polyvinyl alcohol, gum tragacanth, gum karaya, hydroxy propyl cellulose, methyl cellulose and sodium alginate, Laponite CP or SP, which are each synthetic inorganic complex silicate clays sold under trademark by Laporte Industries, Ltd., and magnesium aluminum silicate gel. Iota carrageenan is preferred. The solid portion or gelling agent of the vehicle is typically present in an amount of about 0.5-5% by weight of the toothpaste and preferably about 0.5-2% by weight.

Any suitable substantially water-insoluble polishing agent may be added to the dentifrice vehicle. There is a relatively large number of such materials known in the art. Representative materials include, for example, insoluble sodium metaphosphate, dicalcium phosphate, tricalcium phosphate, hydrated alumina, magnesium carbonate, calcium carbonate, calcium pyrophosphate, calcium sulfate, bentonite, alumina, aluminum silicate, zirconium silicates, silica, including suitable mixtures thereof. In general, these polishing agents will comprise a major portion by weight of the solid ingredients. Insoluble sodium metaphosphate, hydrated alumina, dicalcium phosphate and silica are preferred. The polishing agent content is variable, but will generally be up to about 75% by weight of the total composition, generally about 20–75%, although, even lower amounts of polishing agent can be employed.

Any suitable surface-active or detersive material may be incorporated in the dentifrice vehicle. Such compatible materials are desirable to provide detersive and foaming properties depending upon the specific type of surface-active material selected. These detergents are water-soluble organic compounds usually, and may be anionic, non-ionic, or cationic in structure. It is preferred to use the water-soluble non-soap or synthetic organic detergents. Suitable detersive materials are known and include, for example, the water-soluble anionic salts of higher fatty acid monoglyceride monosulfate detergent (e.g., sodium coconut fatty acid monoglyceride monosulfate), higher alkyl sulfates (e.g., sodium lauryl sulfate), alkyl aryl sulfonate (e.g., sodium dodecyl benzene sulfonate), higher fatty acid esters of 1,2-dihydroxypropane sulfonate) and the like. Sodium lauryl sulfate is preferred. Other suitable surface active materials include nonionic surface active materials such as condensates of ethylene oxide with propylene oxide condensates of propylene glycol ("Pluronics"). Among nonionic surface active agents, Pluronic 127 (Wyandotte) is preferred.

The various surface-active materials may be used in any suitable amount, generally from about 0.05 to about 10% by weight and preferably from about 0.5 to 5% by weight of the dentifrice composition.

The dentifrice of this invention may also contain conventional ingredients such as coloring or whitening agents such as titanium dioxide, preservatives such as sodium benzoate, flavoring and/or sweetening materials, fluorides such as sodium fluoride, stannous fluoride and sodium monofluorophosphate. These additional ingredients may each be added to the dentifrice in minimal amounts of up to 5% by weight, and preferably up to 1%.

The dentifrice is prepared by conventional methods of making toothpaste and gel dentifrice, for instance by for forming a gel with gelling agent and water, adding humectant, mixing in polishing agent and other components except for surfactant and flavor oil and then adding surfactant followed by flavor oil.

The dentifrice may be packaged in a conventional plastic laminate or metal tube or a mechanical or pressurized dispenser. It may be applied to dental surfaces from a toothbrush or by a pointed-type applicator directly to the sensitive area.

The following examples are further illustrative of the nature of the present invention, but it is understood that the invention is not limited thereto. All amounts and proportions referred to herein and in the appended claims are by weight unless otherwise indicated.

EXAMPLE 1

Water slurries containing the indicated concentrations of Gelwhite GP montmorillonite clay are prepared and the flow rates of fluid through dentinal tubules are determined.

| Concentration of Clay | Dentinal Fluid Flow Through Dentinal Tubules (% of Control Value) |
| --- | --- |
| 0.0 (Control) | 100 |
| 0.5 | 46 |
| 1.0 | 36 |
| 3.0 | 23 |
| 5.0 | 23 |

The clay effectively reduces fluid flow through dentinal tubules, thereby producing outstanding reduction in dentine permeability and sensitivity.

EXAMPLE 2

Fluid flow rate through dentinal tubules is determined using water slurries of clay and polycarboxylate (Gantrez S-Y from GAF Corp.)

| Concentration of Clay | Gantrez S-97 | Dentinal Fluid Flow Rate % Through Dentinal Tubules |
| --- | --- | --- |
| 0.0 | 0.0 | 100 |
| 1.0 | 0.5 | 20 |
| 2.0 | 1.0 | 15 |
| 3.0 | 1.5 | 11 |

Clay and polycarboxylate effect great fluid flow reductions through dentinal tubules, thereby producing outstanding reductions in dentine permeability and sensitivity.

EXAMPLE 3

The following sensitive teeth dentifrices are prepared:

|  | Parts A | Parts B |
| --- | --- | --- |
| Water | 33.64 | 32.14 |
| Sorbitol | 11.90 | 11.90 |
| Glycerin | 10.00 | 10.00 |
| Sodium Monofluorophosphate | 0.76 | 0.76 |
| Titanium dioxide | 0.40 | 0.40 |
| Sodium Saccharin | 0.20 | 0.20 |
| Sodium Benzoate | 0.50 | 0.50 |
| Iota Carrageenan | 1.10 | 1.10 |
| Sodium Insoluble Metaphosphate | 30.00 | 30.00 |
| Gelwhite GP (ECCA) | 3.00 | 3.00 |
| Gantrez S-97 (GAF) | — | 1.50 |
| Anhydrous Dicalcium Phosphate | 5.00 | 5.00 |
| Hydrated Alumina | 1.00 | 1.00 |
| Sodium Lauryl Sulfate | 1.50 | 1.50 |
| Flavor | 1.00 | 1.00 |

In variants, sodium lauryl sulfate is replaced by Pluronic 127 nonionic block copolymer of polyoxyethylene/ polyoxypropylene.

EXAMPLE 4

The following sensitive teeth dentifrice is prepared:

|  | Parts |
| --- | --- |
| Glycerin | 25.00 |

-continued

|  | Parts |
| --- | --- |
| Viscarin | 0.60 |
| Sodium Saccharin | 0.30 |
| Sodium monofluorophosphate | 0.76 |
| Sorbitol (70%) | 33.59 |
| Polyethylene Glycol 600 | 3.00 |
| Titantium dioxide | 0.50 |
| Gelwhite GP (ECCA) | 3.00 |
| Water | 12.50 |
| Silica Polishing Agent (Zeo 113-J. M. Huber) | 18.00 |
| Sodium Lauryl Sulfate | 1.75 |
| Flavor | 1.00 |

This invention has been described with respect to certain preferred embodiments and it will be understood that modifications and variations thereof obvious to those skilled in the art are to be included within the purview of this application and the scope of the appended claims.

I claim:

1. A dentifrice comprising at least about 0.1% by weight of montmorillonite, clay in a dentifrice vehicle and about 0.1-3% by weight of a polymeric polycarboxylate.

2. The dentifrice claimed in claim 1 wherein said polymeric polycarboxylate is present in amount of about 0.5-1.5% by weight and is a linear polymeric polycarboxylate having a molecular weight of about 1,000 to about 1,000,000.

3. The dentifrice claimed in claim 2 wherein said linear polymeric polycarboxylate is maleic anhydride-methyl vinyl ether copolymer having a molecular weight of about 30,000 to about 1,000,000.

4. The dentifrice claimed in claim 1 wherein said montmorillonite clay is present in amount of about 0.1-10% by weight.

5. The dentifrice claimed in claim 4 wherein said montmorillonite clay is present in amount of about 0.5-5% by weight.

6. A method for desensitizing hypersensitive dentin by applying thereto a dentifrice composition comprising at least about 0.1% by weight of montmorillonite clay and about 0.1-3% by weight of a polymeric polycarboxylate.

7. The method claimed in claim 6 wherein said polymeric polycarboxylate is present in amount of about 0.5-1.5% by weight and is a linear polymeric polycarboxylate having a molecular weight of about 1,000 to about 1,000,000.

8. The method claimed in claim 7 wherein said linear polymeric polycarboxylate is maleic anhydride-methyl vinyl ether copolymer having a molecular weight of about 30,000 to about 1,000,000.

9. The method claimed in claim 6 wherein said montmorillonite clay is present in amount of about 0.1-10% by weight.

10. The method claimed in claim 9 wherein said montmorillonite clay is present in amount of about 0.5-5% by weight.

* * * * *